(12) United States Patent
Ponzi

(10) Patent No.: US 6,171,277 B1
(45) Date of Patent: Jan. 9, 2001

(54) BI-DIRECTIONAL CONTROL HANDLE FOR STEERABLE CATHETER

(75) Inventor: Dean M. Ponzi, Glendora, CA (US)

(73) Assignee: Cordis Webster, Inc., Diamond Bar, CA (US)

(*) Notice: Under 35 U.S.C. 154(b), the term of this patent shall be extended for 0 days.

(21) Appl. No.: 09/130,359

(22) Filed: Aug. 7, 1998

Related U.S. Application Data

(63) Continuation-in-part of application No. 08/982,113, filed on Dec. 1, 1997.

(51) Int. Cl.$^7$ ............ A61M 37/00; A61M 25/01; A61B 17/20
(52) U.S. Cl. ............ 604/95.04; 604/528; 604/22
(58) Field of Search ............ 604/20–22, 95.04, 604/523, 528; 600/434, 149; 607/122

(56) References Cited

U.S. PATENT DOCUMENTS

| | | | |
|---|---|---|---|
| Re. 34,502 | 1/1994 | Webster, Jr. | 607/125 |
| 3,470,876 | 10/1969 | Barchilon | 128/348 |
| 3,605,725 | 9/1971 | Bentov | 128/2.05 R |
| 3,625,200 | 12/1971 | Muller | 128/2.05 R |
| 3,892,228 * | 7/1975 | Mitsui | 128/4 |
| 4,191,196 | 3/1980 | Bradley et al. | 128/733 |
| 4,203,430 | 5/1980 | Takahashi | 128/4 |
| 4,207,873 | 6/1980 | Kruy | 128/6 |
| 4,233,991 | 11/1980 | Bradley et al. | 128/733 |
| 4,586,923 | 5/1986 | Gould et al. | 604/95 |
| 4,685,457 | 8/1987 | Donenfeld | 128/207.14 |
| 4,753,223 | 6/1988 | Bremer | 128/4 |
| 4,826,087 | 5/1989 | Chinery | 239/551 |
| 4,838,859 | 6/1989 | Strassmann | 604/95 |
| 4,921,482 | 5/1990 | Hammerslag et al. | 604/95 |
| 4,960,134 | 10/1990 | Webster, Jr. | 128/786 |
| 4,998,916 | 3/1991 | Hammerslag et al. | 604/95 |
| 5,019,090 | 5/1991 | Pinchuk | 606/194 |
| 5,037,391 | 8/1991 | Hammerslag et al. | 604/95 |
| 5,108,368 | 4/1992 | Hammerslag et al. | 604/95 |

(List continued on next page.)

Primary Examiner—Sharon Kennedy
Assistant Examiner—Michael J. Hayes
(74) Attorney, Agent, or Firm—Christie, Parker & Hale, LLP

(57) ABSTRACT

A bidirectional steerable catheter comprises a catheter body, a tip section, and a control handle. The catheter body has a tubular wall, proximal and distal ends, and at least one lumen extending therethrough. The tip section comprises flexible tubing having proximal and distal ends and at least one lumen extending therethrough. The proximal end of the tip section is fixedly attached to the distal end of the catheter body. The control handle is mounted at its distal end to the proximal end of the catheter body. The control handle comprises a housing having proximal and distal ends. Rotatably mounted within the housing is a generally-circular spur gear having gear teeth about its outer circumference. A pair of spaced apart rack gears are slidably mounted longitudinally on diametrically opposed sides of the spur gear within the housing. Each rack gear has an interior edge generally facing the interior edge of the other rack gear and comprises gear teeth along its interior edge for engaging the gear teeth of the spur gear. Each rack gear is longitudinally movable between first and second positions. Proximal movement of one rack gear results in rotational movement of the spur gear, and correspondingly distal movement of the other rack gear. Two puller wires extend from the control handle, through a lumen in the catheter body and into an off axis lumen in the tip section. The distal end of each puller wire is fixedly attached to the tip section, and the proximal end of each puller wire is anchored to a separate associated rack gear in the control handle. Proximal movement of a rack gear and its associated puller wire relative to the catheter body results in deflection of the tip section in the direction of the off axis lumen into which that puller wire extends.

22 Claims, 12 Drawing Sheets

U.S. PATENT DOCUMENTS

| | | | |
|---|---|---|---|
| 5,199,950 | 4/1993 | Schmitt et al. | 604/95 |
| 5,318,525 | 6/1994 | West et al. | 604/95 |
| 5,358,478 | 10/1994 | Thompson et al. | 604/95 |
| 5,359,994 | 11/1994 | Krauter et al. | 128/4 |
| 5,364,351 | 11/1994 | Heinzelman et al. | 604/95 |
| 5,368,564 | 11/1994 | Savage | 604/95 |
| 5,383,923 | 1/1995 | Webster, Jr. | 607/125 |
| 5,397,304 | 3/1995 | Truckai | 604/95 |
| 5,397,321 | 3/1995 | Houser et al. | 606/41 |
| 5,419,767 | 5/1995 | Eggers et al. | 604/114 |
| 5,431,168 | 7/1995 | Webster, Jr. | 128/658 |
| 5,441,483 | 8/1995 | Avitall | 604/95 |
| 5,456,664 | 10/1995 | Heinzelman et al. | 604/95 |
| 5,492,119 | 2/1996 | Abrams | 128/642 |
| 5,507,725 | 4/1996 | Savage et al. | 604/95 |
| 5,531,686 | 7/1996 | Lundquist et al. | 604/95 |
| 5,588,964 | 12/1996 | Imran et al. | 604/95 |
| 5,626,136 | 5/1997 | Webster et al. | 128/642 |
| 5,656,029 | 8/1997 | Imran et al. | 604/95 |
| 5,656,030 | 8/1997 | Hunjan et al. | 604/95 |
| 5,681,280 | 10/1997 | Rusk et al. | 604/95 |
| 5,741,320 | 4/1998 | Thornton et al. | 607/122 |
| 5,792,074 * | 8/1998 | Turkel et al. | 600/569 |
| 5,803,083 * | 9/1998 | Buck et al. | 128/660.03 |

* cited by examiner

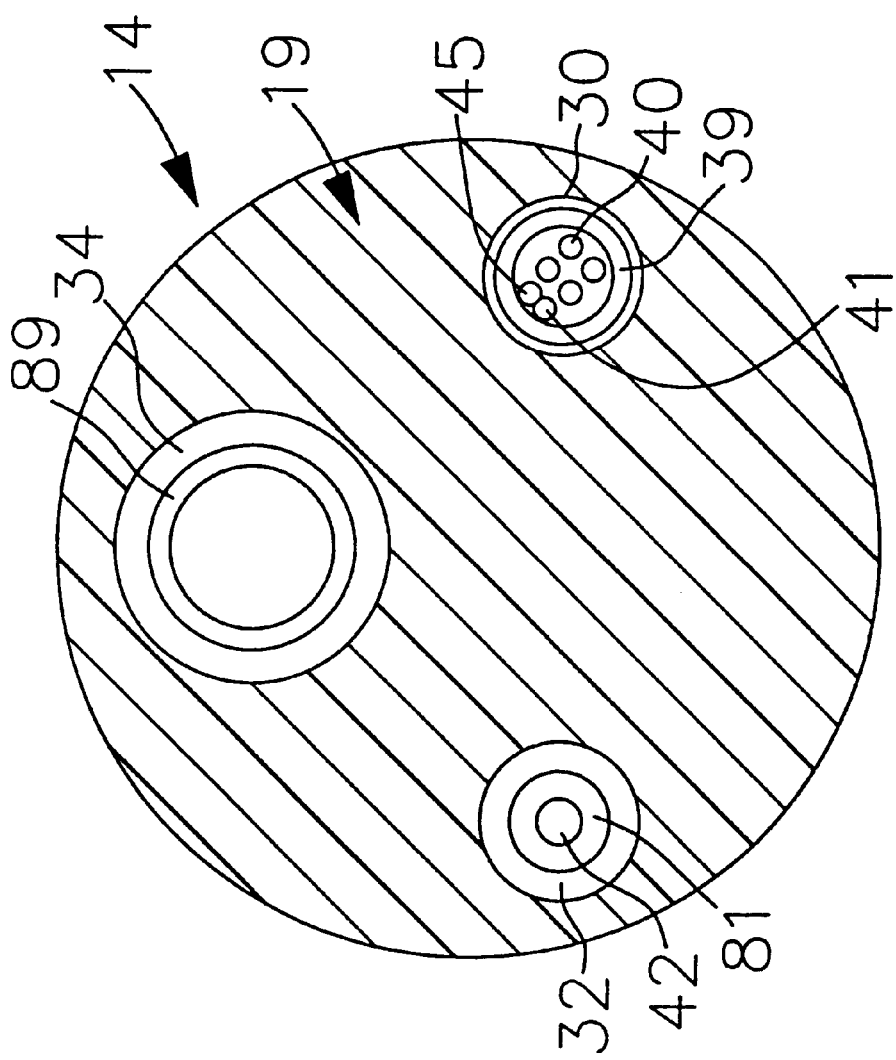

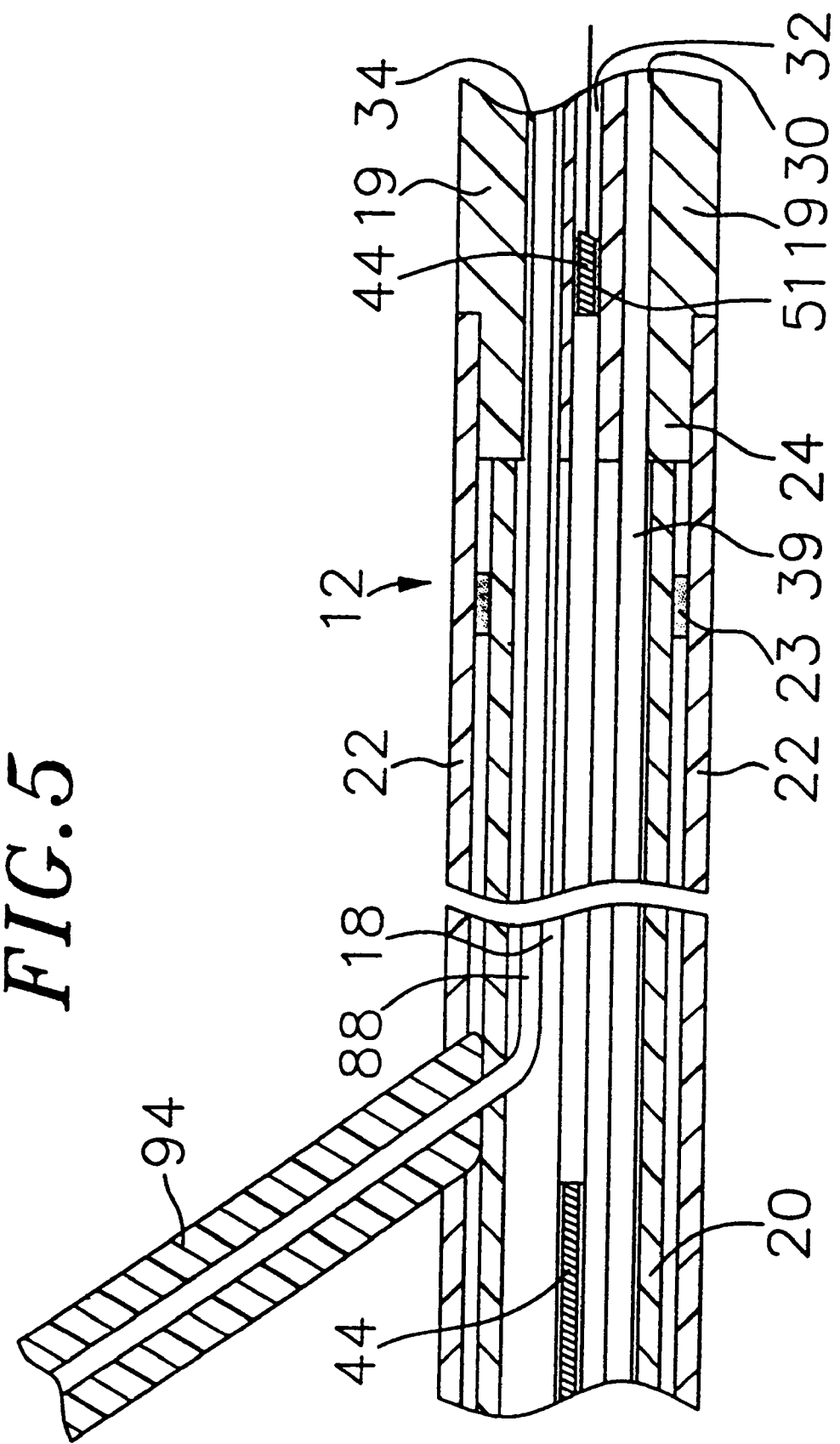

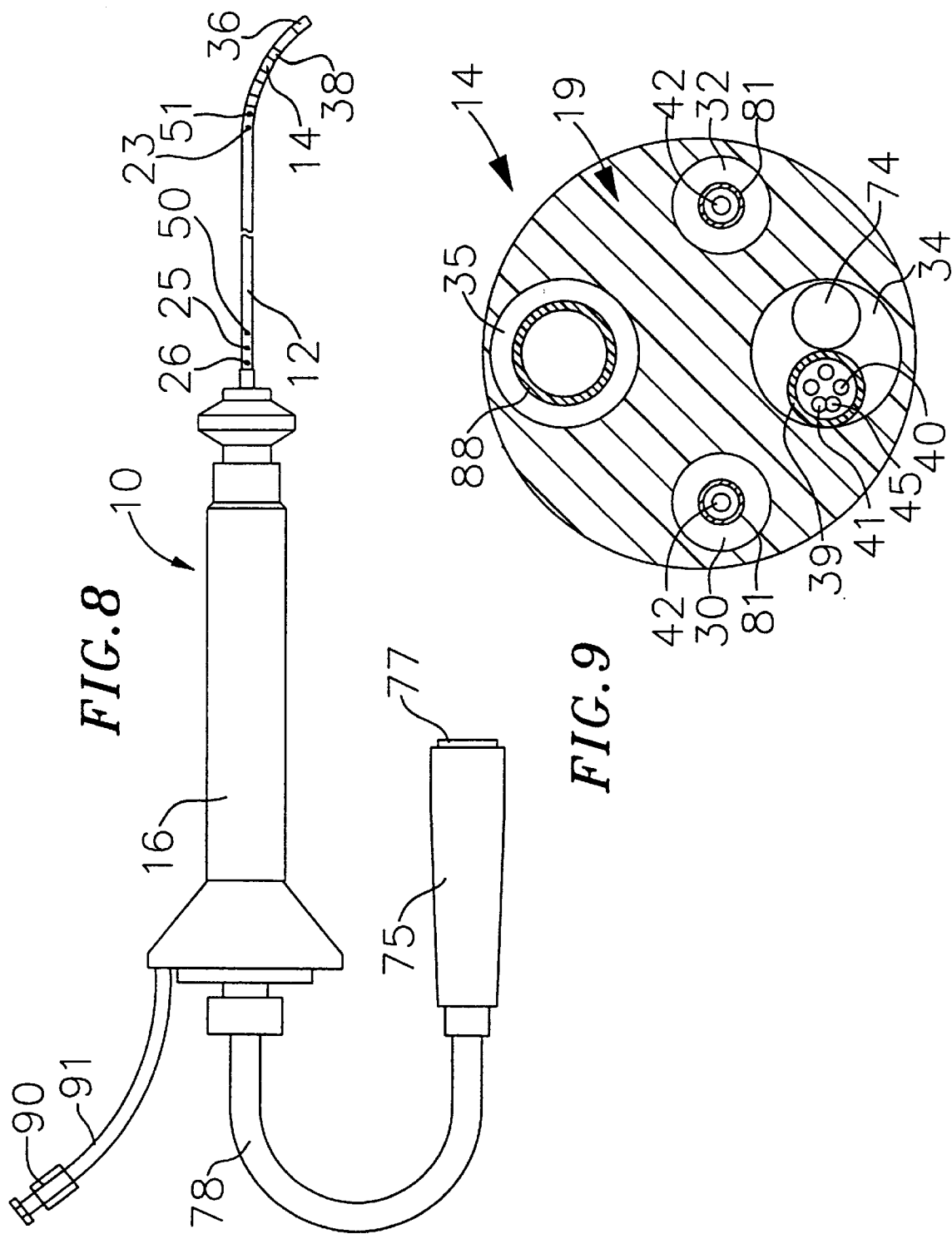

BI-DIRECTIONAL CONTROL HANDLE FOR STEERABLE CATHETER

This application is a Continuation-In-Part of Ser. No. 08/982,113, filed Dec. 1, 1997.

FIELD OF THE INVENTION

The present invention relates to improved bidirectional steerable catheters, and more particularly to catheters having bidirectional control handles.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

The design described in RE 34,502 is generally limited to a catheter having a single puller wire. If a bidirectional catheter is desired, i.e., a catheter that can be deflected in more than one direction without rotating the catheter body, more than one puller wire becomes necessary. When two puller wires are used, however, it is undesirable for both wires to be moved simultaneously. The handle design disclosed in RE 34,502 is not suitable for a two puller wire system. Accordingly, a need exists for a control handle capable of independently moving each of two puller wires but preventing simultaneous movement of the puller wires.

SUMMARY OF THE INVENTION

The present invention provides a bidirectional steerable catheter that is particularly useful in ablation procedures. The catheter comprises a catheter body, a tip section, and a control handle. The catheter body has a tubular wall, proximal and distal ends, and at least one lumen extending therethrough. The tip section comprises flexible tubing having proximal and distal ends and at least one lumen extending therethrough. The proximal end of the tip section is fixedly attached to the distal end of the catheter body.

The control handle is mounted at its distal end to the proximal end of the catheter body. The control handle comprises a housing having proximal and distal ends. Rotatably mounted within the housing is a generally-circular spur gear having gear teeth about its outer circumference. A pair of spaced apart rack gears are slidably mounted longitudinally on diametrically opposed sides of the spur gear within the housing. Each rack gear has an interior edge generally facing the interior edge of the other rack gear and comprises gear teeth along its interior edge, which engage the gear teeth of the spur gear. Each rack gear is longitudinally movable between first and second positions. In this arrangement, proximal movement of one rack gear results in rotational movement of the spur gear, and correspondingly distal movement of the other rack gear.

Two puller wires extend from the control handle, through a lumen in the catheter body and into separate, preferably diametrically opposed, off axis lumens in the tip section. The distal end of each puller wire is fixedly attached to the tip section, and the proximal end of each puller wire is fixedly attached to a separate associated rack gear in the control handle. Proximal movement of a rack gear and its associated puller wire relative to the catheter body results in deflection of the tip section in the direction of the off axis lumen into which that puller wire extends.

Preferably a manually movable member is fixedly attached to one of the rack gears so that the movable member is accessible, at least in part, on the exterior of the handle housing. The user can thus move one of the rack gears by longitudinally sliding the manually movable member.

DESCRIPTION OF THE DRAWINGS

These and other features and advantages of the present invention will be better understood by reference to the following detailed description when considered in conjunction with the accompanying drawings wherein:

FIG. 4 is a longitudinal cross-sectional view of the tip section illustrated in FIG. 3 across line 4—4.

FIG. 5 is a side cross-sectional view of an alternative embodiment of a catheter body according to the invention having a side arm for an infusion tube.

FIG. 8. is a side cross-sectional view of an alternative embodiment of a catheter containing an electromagnetic sensor.

FIG. 9 is a longitudinal cross-sectional view of the proximal end of catheter tip section for a bidirectional catheter embodiment according to the invention.

DETAILED DESCRIPTION

In a particularly preferred embodiment of the invention, there is provided a steerable catheter having an irrigated tip. As shown in FIGS. 1–6, catheter 10 comprises an elongated catheter body 12 having proximal and distal ends, a tip section 14 at the distal end of the catheter body 12, and a control handle 16 at the proximal end of the catheter body 12.

Figure 1:
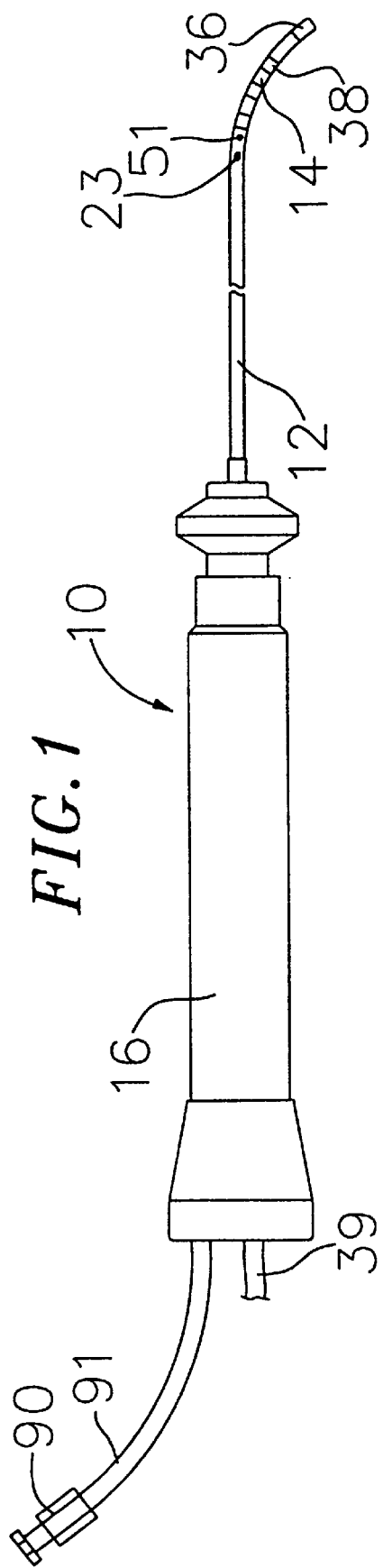
FIG. 1 is a side cross-sectional view of an embodiment of the catheter of the invention.

With reference to FIG. 1, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the single lumen 18 of the catheter body 12 are lead wires, an infusion tube, and a compression coil through which a puller wire extends. A single lumen catheter body is preferred over a multi-lumen body because it has been found that the single lumen body permits better tip control when rotating the catheter. The single lumen permits the lead wires, infusion tube, and the puller wire surrounded by the compression coil to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

A particularly preferred catheter has an outer wall 22 with an outer diameter of from about 0.090 inch to about 0.94 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch.

Figure 3:
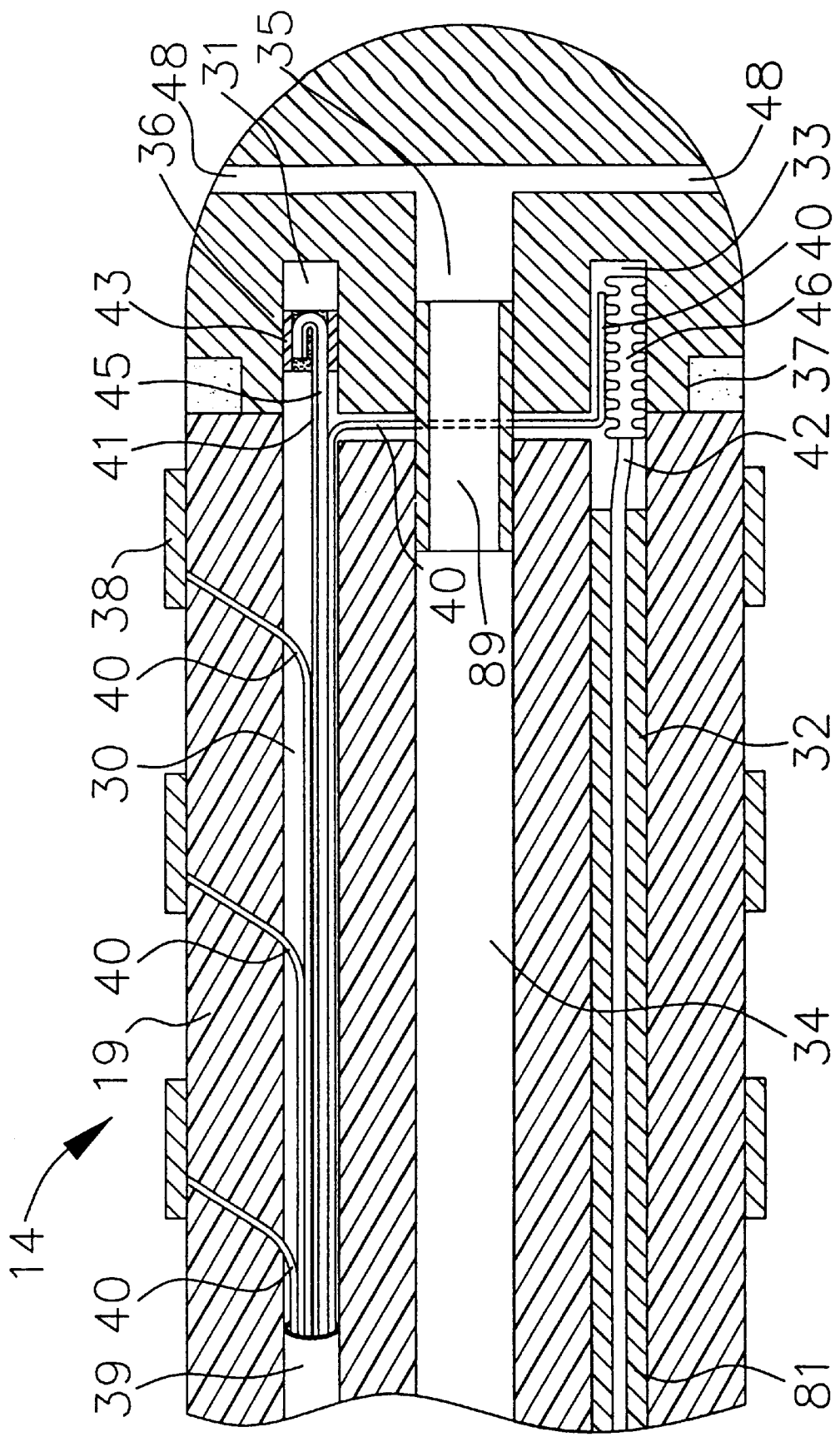
FIG. 3 is a side cross-sectional view of a catheter tip section showing an embodiment having a fluid passage comprising an axial branch and multiple transverse branches.

As shown in FIGS. 3 and 4, the tip section 14 comprises a short section of tubing 19 having three lumens. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french, more preferably 7 french. The size of the lumens is not critical. In a particularly preferred embodiment, the tip section 14 has an outer diameter of about 7 french (0.092 inch) and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.036 inch.

Figure 2:
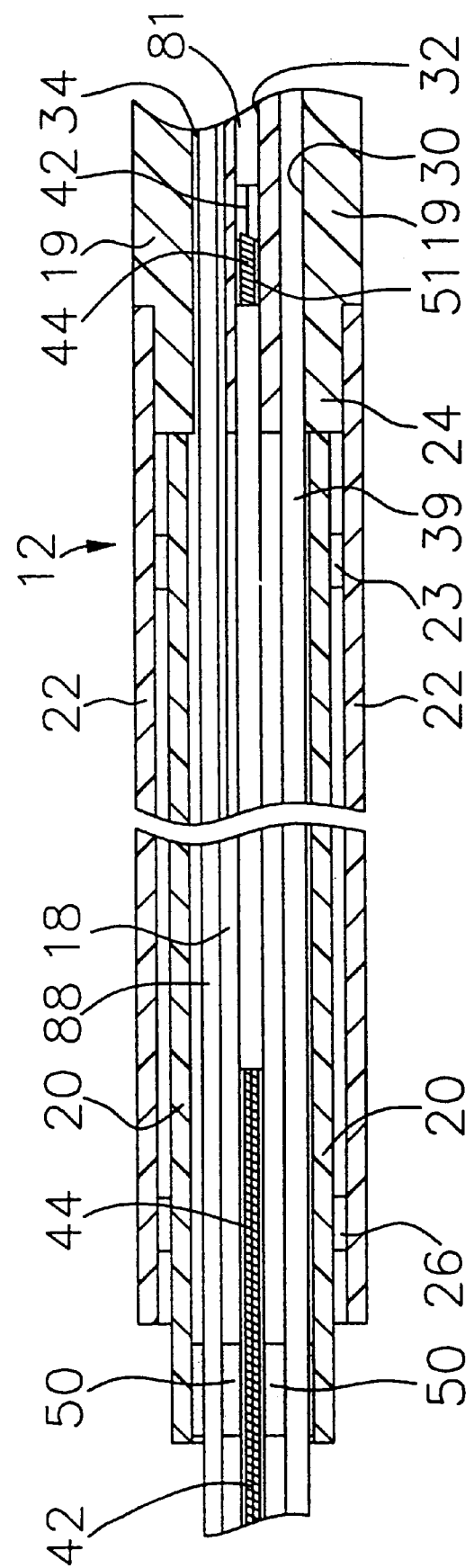
FIG. 2 is a side cross-sectional view of a catheter body according to the invention, including the junction between the catheter body and tip section.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and tip section, which allows this junction to bend smoothly without folding or kinking. A catheter having such a spacer is described in U.S. Pat. No. 5,964,757, entitled "Steerable Direct Myocardial Revascularization Catheter", the disclosure of which is incorporated herein by reference.

At the distal end of the tip section 14 is a tip electrode 36. Preferably the tip electrode 36 has a diameter about the same as the outer diameter of the tubing 19. As illustrated in FIG. 3, the tip electrode 36 is generally solid, having a fluid passage 35 and a pair of blind holes 31 and 33 that correspond in size and location to the three lumens 34, 30 and 32 respectively in the tip section 14. The blind holes 31 and 33 extend from the proximal end of the tip electrode 36, but do not extend through to the distal end of the tip electrode. In the embodiment shown, the fluid passage 35 comprises an axial branch and six transverse branches 48 that extend radially from the distal end of the axial branch to the outer surface of the tip electrode 36. It is understood that the configuration of the fluid passage may vary as desired.

A preferred tip electrode has an effective length, i.e., from its distal end to the distal end of the tubing, of about 3.5 mm, and an actual length, i.e., from its distal end to its proximal end, of about 4.0 mm. As shown in FIG. 3, this preferred tip electrode 36 is attached to the tubing 19 by creating a notch 37 in the proximal end of the tip electrode 36, placing the proximal end of the tip electrode on the distal end of the tubing 19, and filling the notch 37 with glue. The wires and tubes that extend into the tip electrode 36 help to keep the tip electrode in place on the tip section.

In the embodiment shown, there are three ring electrodes 38 mounted on the tubing 19 proximal to the tip electrode 36. It is understood that the presence and number of ring electrodes 38 may vary as desired. Each ring electrode 38 is slid over the tubing 19 and fixed in place by glue or the like.

The tip electrode 36 and ring electrodes 38 can be made of any suitable material, and are preferably machined from platinun-iridium bar (90% platinum/10% iridium).

The tip electrode 36 and ring electrodes 38 are each connected to a separate lead wire 40. The lead wires 40 extend through the first lumen 30 of tip section 14, the central lumen 18 of the catheter body 12, and the control handle 16, and terminate at their proximal end in an input jack (not shown) that may be plugged into an appropriate monitor (not shown). The portion of the lead wires 40 extending through the central lumen 18 of the catheter body 12, control handle 16 and proximal end of the tip section 14 are enclosed within a protective sheath 39, which can be made of any suitable material, preferably polyimide. The protective sheath 39 is anchored at its distal end to the proximal end of the tip section 14 by gluing it in the second lumen 32 with polyurethane glue or the like.

The lead wires 40 are attached to the tip electrode 36 and ring electrodes 38 by any conventional technique. Connection of a lead wire 40 to the tip electrode 36 is accomplished, for example, by welding the lead wire 40 into the second hole 33 in the tip electrode.

Connection of a lead wire 40 to a ring electrode 38 is preferably accomplished by first making a small hole through the tubing 19. Such a hole can be created, for example, by inserting a needle through the tubing 19 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A temperature sensing means is provided for the tip electrode 36 and, if desired, the ring electrodes 38. Any conventional temperature sensing means, e.g., a thermocouple or thermistor, may be used. With reference to FIG. 3, a preferred temperature sensing means for the tip electrode 36 comprises a thermocouple formed by a wire pair. One wire of the wire pair is a copper wire 41, e.g., a number 40 copper wire. The other wire of the wire pair is a constantan wire 45, which gives support and strength to the wire pair. The wires 41 and 45 of the wire pair are electrically isolated from each other except at their distal ends where they contact and are twisted together, covered with a short piece of plastic tubing 43, e.g., polyimide, and covered with epoxy. The plastic tubing 43 is then attached in the first blind hole 31 of the tip electrode 36, by polyurethane glue or the like. The wires 41 and 45 extend through the first lumen 31 in the tip section 14. Within the catheter body 12 the wires 41 and 45 extend through the protective sheath 39 with the lead wires 40. The wires 41 and 45 then extend out through the control handle 16 and to a connector (not shown) connectable to a temperature monitor (not shown).

Alternatively, the temperature sensing means may be a thermistor. A suitable thermistor for use in the present invention is Model No. AB6N2-GC14KA143E/37C sold by Thermometrics (New Jersey).

A puller wire 42 extends through the catheter body 12, is anchored at its proximal end to the control handle 16, and is anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated within the catheter body 12 in surrounding relation to the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. The Teflon® coating on the puller wire 42 allows it to slide freely within the compression coil 44. If desired, particularly if the lead wires 40 are not enclosed by a protective sheath 39, the outer surface of the compression coil 44 can be covered by a flexible, non-conductive sheath, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The puller wire 42 extends into the second lumen 32 of the tip section 14. The puller wire 42 is anchored at its distal end to the tip electrode 36 within the second blind hole 33. A preferred method for anchoring the puller wire 42 within the tip electrode 36 is by crimping metal tubing 46 to the distal end of the puller wire 42 and soldering the metal tubing 46 inside the second blind hole 33. Anchoring the puller wire 42 within the tip electrode 36 provides additional support, reducing the likelihood that the tip electrode 36 will fall off the tip section 14. Alternatively, the puller wire 42 can be attached to the side of the tip section 14. Within the second lumen 32 of the tip section 14, the puller wire 42 extends through a plastic, preferably Teflon®, sheath 81, which prevents the puller wire 42 from cutting into the wall of the tip section 14 when the tip section is deflected.

An infusion tube is provided within the catheter body 12 for infusing fluids, e.g., saline, to cool the tip electrode 36.

The infusion tube may also be used to infuse drugs or to collect tissue or fluid samples. The infusion tube may be made of any suitable material, and is preferably made of polyimide tubing. A preferred infusion tube has an outer diameter of from about 0.32 inch to about 0.036 inch and an inner diameter of from about 0.28 inch to about 0.032 inch.

Figure 3A:
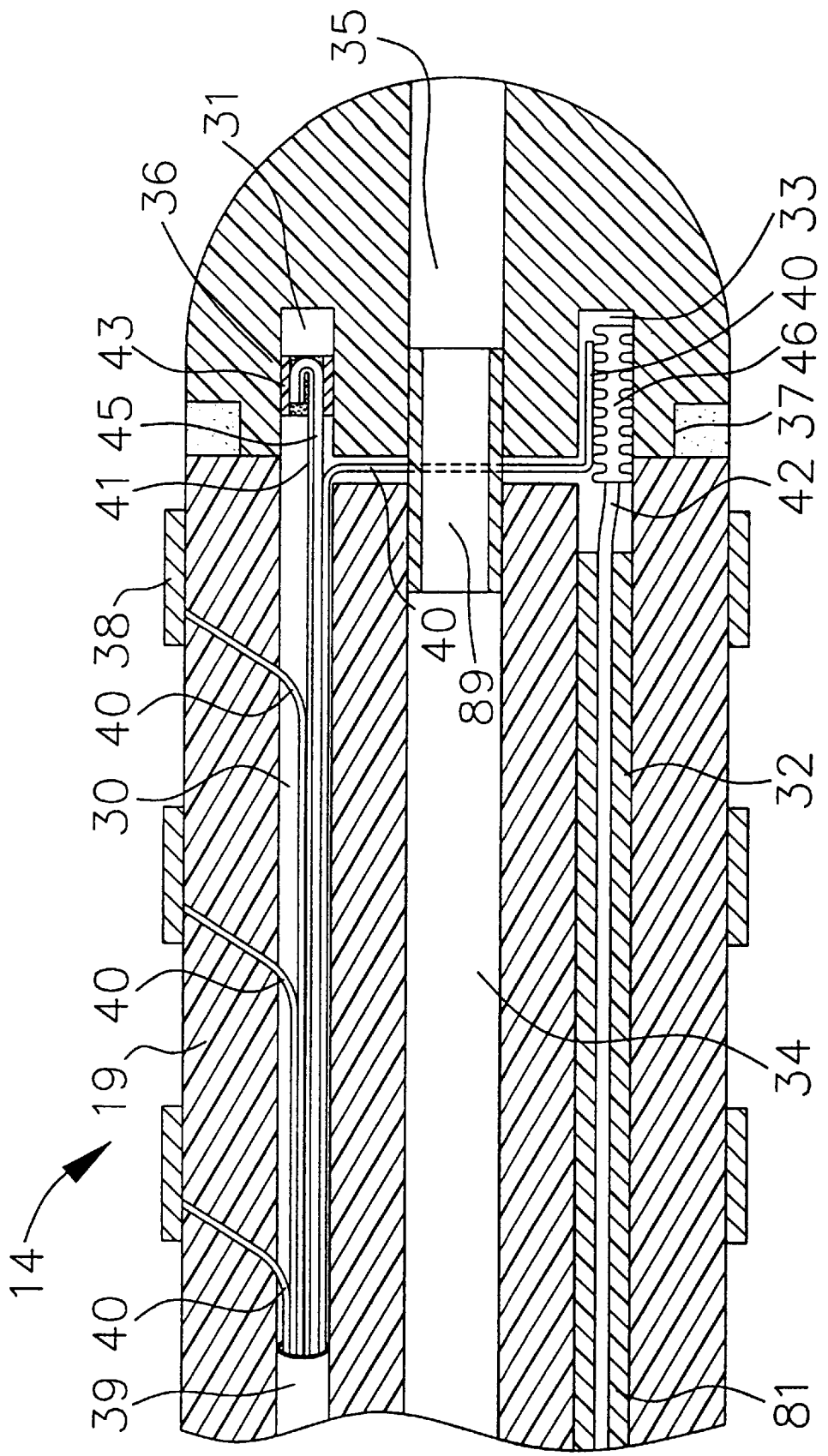
FIG. 3A is a side cross-sectional view of a catheter tip section showing an embodiment wherein the fluid passage comprises a longitudinal hole.

With reference to FIGS. 2, 3 and 4, a first infusion tube segment 88 extends through the central lumen 18 of the catheter body 12 and terminates in the proximal end of the third lumen 34 of the tip section 14. The distal end of the first infusion tube segment 88 is anchored in the third lumen 34 by polyurethane glue or the like. The proximal end of the first infusion tube segment 88 extends through the control handle 16 and terminates in a luer hub 90 or the like at a location proximal to the control handle. A second infusion tube segment 89 is provided at the distal end of the third lumen 34 and extends into the fluid passage 35 of the tip electrode 36. The second infusion tube segment 89 is anchored within the third lumen 34 and the fluid passage 35 by polyurethane glue or the like. The second infusion tube segment 89, like the puller wire 42, provides additional support for the tip electrode. In practice, fluid may be injected into the first infusion tube segment 88 through the luer hub 90, and flows through the first infusion tube segment 88, through the third lumen 34, through the second infusion tube segment, into 89 into the fluid passage 35 in the tip electrode 36, and out the transverse branches 48 of the fluid passage 35 in the tip electrode. Again, the fluid passage may have other configurations as desired. For example, the fluid passage 35 may form a longitudinal hole that extends out the distal end of the tip electrode 36, as shown in FIG. 3A, or the tip electrode 36 may be porous enough to allow fluids to pass to the outer surface of the tip electrode, the interconnecting pores forming the fluid passage.

In an alternative arrangement, as shown in FIG. 5, a single lumen side arm 94 is fluidly connected to the central lumen 18 near the proximal end of the catheter body 12. The first infusion tube segment 88 extends through the catheter body 12 and out the side arm 94, where it terminates in a luer hub 90 or the like. The side arm 94 is preferably made of the same material as the outer wall 22, but preferably has a greater thickness, e.g., 0.055 inch. Where the side arm 94 meets the catheter body 12, a molded joint can be provided to provide additional strength and support. The molded joint can be made of any suitable biocompatable material, and is preferably made of polyurethane.

Figure 6:
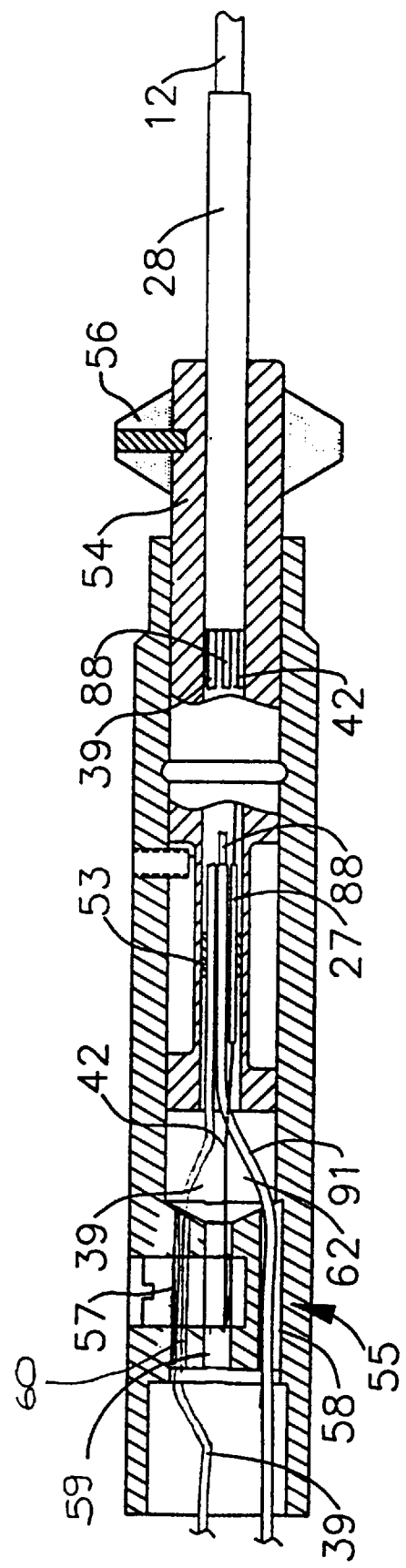
FIG. 6 is a side cross-sectional view of an embodiment of a catheter control handle according to the invention.

Longitudinal movement of the puller wire 42 relative to the catheter body 12, which results in deflection of the tip section 14, is accomplished by suitable manipulation of the control handle 16. As shown in FIG. 6, the distal end of the control handle 16 comprises a piston 54 with a thumb control 56 for manipulating the puller wire 42. The proximal end of the catheter body 12 is connected to the piston 54 by means of a shrink sleeve 28.

The puller wire 42, lead wires 40, thermocouple wires 41 and 45, and first infusion tube segment 88 extend through the piston 54. The puller wire 42 is anchored to an anchor pin 57, located proximal to the piston 54. Within the control handle 16, the lead wires 40 and thermocouple wires 41 and 45 are within the protective sheath 39. Within the piston 54, the first infusion tube segment 88 extends into another protective sheath 91, preferably made of polyurethane, similar to the side arm 94, described above. The protective sheathes 39 and 91 are anchored to the piston 54, preferably by polyurethane glue or the like at a glue joint 53, allowing the first infusion tube segment 88, lead wires 40 and thermocouple wires 41 and 45 longitudinal movement within the control handle 16 so that they does not break when the piston 54 is adjusted to manipulate the puller wire 42. Within the piston 54, the puller wire 42 extends through a transfer tube 27, preferably a polyimide tube, to allow longitudinal movement of the puller wire near the glue joint 53.

The piston 54 lies within the barrel 55 of the control handle. The barrel 55 is generally solid having a piston chamber for receiving the piston 54. Extending proximally from the piston chamber are three longitudinal holes 58, 59 and 60 and a transverse hole for receiving the anchor pin 57. The second longitudinal hole 59 is in communication with the transverse hole. The first infusion tube segment 88 within the protective sheath 91 extends through the first longitudinal hole 58 while the lead wires 40. The puller wire 42 extends through the second longitudinal hole 59 and is anchored to the anchor pin 57 in the transverse hole. The thermocouple wires 41 and 45 within the protective sheath 39 extend through the third longitudinal hole 60. Between the distal end of the longitudinal holes 58, 59 and 60 and the proximal end of the piston 54, chamber 62 provides additional space to avoid undesirable bending of the first infusion tube segment 88. Preferably the space has a length of at least 0.50 inch and more preferably about from about 0.60 inch to about 0.90 inch.

Figure 7:
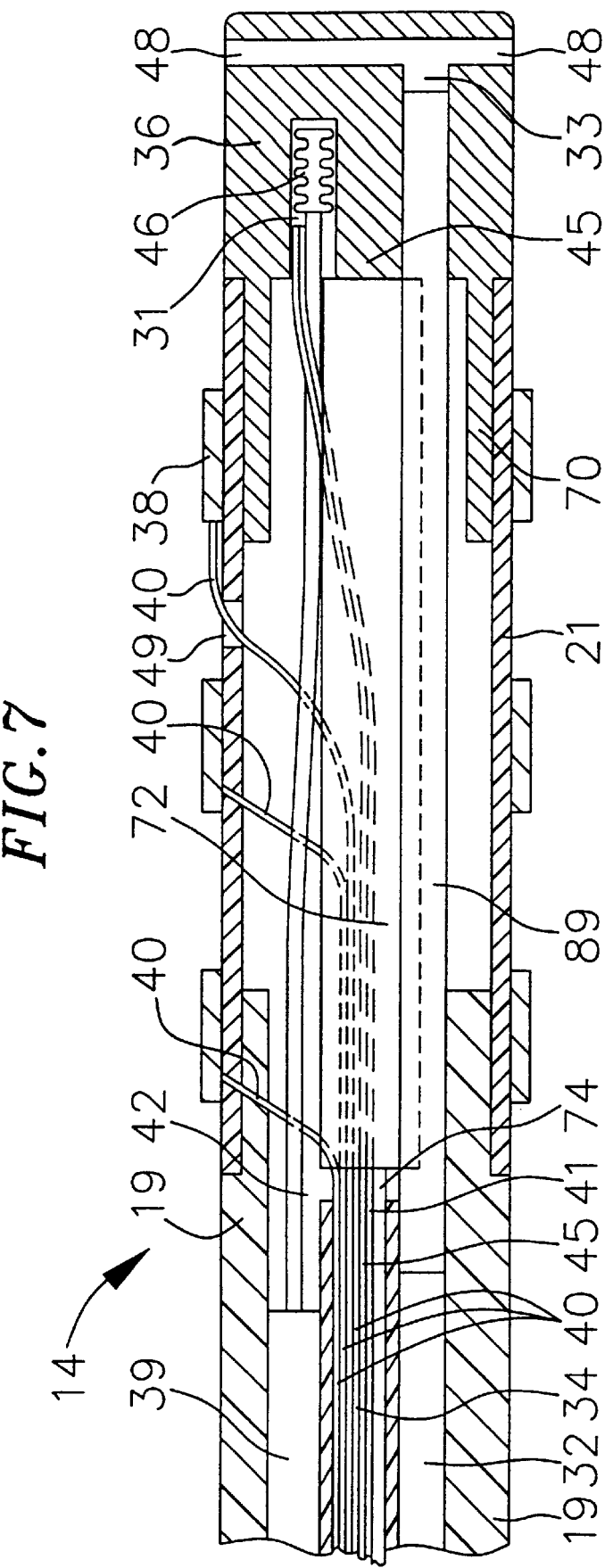
FIG. 7 is a side cross-sectional view of an alternative embodiment of a catheter tip section containing an electromagnetic sensor.

In another preferred embodiment according to the invention, an electromagnetic sensor 72 is located within the distal end of the tip section 14. As shown in FIG. 7, in this embodiment the tip electrode 36 is connected to the tubing 19 of the tip section 14 by means of a plastic housing 21, preferably made of polyetheretherketone (PEEK). The proximal end of the tip electrode 36 is notched circumferentially to form a stem 70, which fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. Preferably the plastic housing is about 1 cm long.

Preferably the tip electrode 36 has a total length of about 7 mm, with the stem 70 having a length of about 3.5 mm (i.e., half the total length of the tip electrode). The distal end of the tip electrode 36 is generally solid with a blind hole 31 and a fluid passage 33 with six transverse branches 48. In the embodiment shown, the stem 70 of the tip electrode 36 is generally hollow.

A second infusion tube segment 89, as described above, extends into and is anchored in the fluid passage 33 of the tip electrode 36. The infusion tube segments 88 and 89 preferably have an outer diameter of about from 0.029 inch to about 0.33 inch and an inner diameter of from about 0.025 inch to about 0.029 inch.

A puller wire 42 extends into and is anchored in the blind hole 31 of the tip electrode 36. A pair of thermocouple wires 41 and 45, as described above, also extend into and are soldered into the first hole 31 of the tip electrode 36, and the copper wire 41 acts also as a lead wire 40 for the tip electrode. The electromagnetic sensor 72 is positioned within the plastic housing 21 and hollow stem 70 of the tip electrode 36. The sensor 72 is fixedly attached within the tip electrode 36 and the plastic housing 21 by polyurethane glue or the like.

Mounted on the plastic housing 21 are three ring electrodes 38. The presence and number of ring electrodes 38 can vary as desired. Each ring electrode 38 is slid over the plastic housing 21 and fixed in place by glue or the like. Alternatively, one or more ring electrodes 38 can be positioned over the flexible tubing 19 of the tip section 14.

Lead wires are attached to the ring electrodes 38 generally as described above. However, due to the length of the plastic housing 21, the most distal ring electrode 38 is mounted on the plastic housing 21 at a position above the stem 70 of the tip electrode 36. As a result, the lead wire 40 for the most distal ring electrode 38 extends though a hole 49 in the plastic housing 21 that is proximal to the distal ring electrode 38 and stem 70. The lead wire 40 extends a short distance along the outside of the plastic housing 21 and is soldered to the underside of the most distal ring electrode 38. Polyurethane glue or the like is used to cover the exposed section of the lead wire 40 and to fill in the hole 49.

The electromagnetic sensor 72 is connected to a electromagnetic sensor cable 74, which extends through the third lumen 34 of the tip section 14, through the central lumen 18 of the catheter body 12, and into the control handle 16. The electromagnetic sensor cable 74 then extends out the proximal end of the control handle 16 within an umbilical cord 78 to a sensor control module 75 that houses a circuit board (not shown). Alternatively, the circuit board can be housed within the control handle 16, for example, as described in U.S. Pat. No. 5,964,757, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 8. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. Suitable electromagnetic sensor for use with the present invention are described, for example, in U.S. Pat. Nos. 5,558,091, 5,443,489, 5,480,422, 5,546,951, 5,568,809, and 5,391,199 and International Publication No. WO 95/02995, the disclosures of which are incorporated herein by reference. A preferred electromagnetic mapping sensor 72 has a length of from about 6 mm to about 7 mm and a diameter of about 1.3 mm.

To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the catheter containing a second electromagnetic sensor is advanced into the patient's heart. Each sensor comprises three small coils that in the magnetic field generate weak electrical signals indicative of their position in the magnetic field. Signals generated by both the fixed reference sensor and the second sensor in the heart are amplified and transmitted to a computer that analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved. This procedure is repeated until a three-dimensional image of the heart chamber is achieved. A preferred mapping system includes a catheter comprising multiple electrodes and an electromagnetic sensor.

The catheter body 12 is generally similar to that described above, having an open central lumen 18. Preferably, the catheter body 12 in this embodiment does not comprise a stiffening tube 20, however, because additional space is needed within the central lumen 10 to include the electromagnetic sensor cable sensor cable 74. Preferably the catheter body has an outer diameter no greater than about 8 French, more preferably about 7 to about 7.5 French.

The control handle 16 is also generally similar to that described above. However, the electromagnetic sensor cable 74 extends out the proximal end of the control handle 16 where it is connected to the sensor control module 75.

An alternative embodiment of a catheter according to the present invention is a bidirectional catheter containing two puller wires to enhance the ability to manipulate the tip section. As illustrated in FIG. 9, the tip section 14 of this embodiment contains four lumens. For a tip section having a diameter of about 7 French, the diameters of the first lumen 30 and second lumen 32 are similar in size, and are each preferably 0.018 inch. The diameters of the third lumen 34 and fourth lumen 35 are also similar in size and are each preferably 0.029 inch. The tip section 14 carries a tip electrode 36 and ring electrodes 38. A thermocouple, or other temperature sensing means, is provided for the tip electrode 36 as discussed above. The lead wires 40 for the ring electrodes 38, as well as the thermocouple wires 40 and 45, one of which serves as the tip electrode lead wire, extend through the third lumen 34. The tip section 14 also contains an electromagnetic sensor 72, and the electromagnetic sensor cable 74 also extends through the third lumen 34. A first infusion tube segment 88 extends through the control handle 16 and catheter body 12 and into the fourth lumen 35. A second infusion tube segment 89 extends from the distal end of the fourth lumen 35 in the tip section 14 and into the tip electrode 36 in a manner similar to the embodiment described above.

Two puller wires 34 and surrounding compression coils 44 extend from the control handle 16 through the central lumen 18 of the catheter body 12 as described above. Within the tip section 14, one puller wire 34 extends into the first lumen 30 and the other puller wire extends into the second lumen 32. The puller wires 34 then extend into holes in the tip electrode 36 preferably coaxial with the first lumen 30 and second lunen 32 and are anchored within the holes of the tip electrode as described above. Within the tip section 14, the puller wires 34 each extend through a plastic, preferably Teflon®, sheath 81, to prevent the puller wires 42 from cutting into the wall of the tip section 14 when the tip section is deflected The lumens 30 and 32 of the tip section receiving the puller wires may be in adjacent quadrants, but are preferably in opposing quadrants. If desired, the distal ends of one or both of the puller wires may be anchored to the side wall of the catheter tip section for example as described in U.S. patent application Ser. No. 08/924,611, which is incorporated herein by reference. Moreover, the first puller wire may be anchored proximal to the anchor location of the second puller wire.

A particularly preferred catheter construction comprising multiple puller wires including control handle construction is disclosed in U.S. patent application Ser. No. 08/924,611, entitled "Omni-Directional Steerable Catheter", the disclosure of which is incorporated herein by reference. Such application describes a suitable control handle for manipulating two or more puller wires. The described control handle includes a central passage that may be expanded to accommodate the electrode lead wires, electromagnetic sensor cable, optic fiber and even infusion tube. Further, an extension of the handle may be provided to house the circuit board for the electromagnetic sensor, e.g., in the same manner as shown in FIG. 8.

Figure 10:
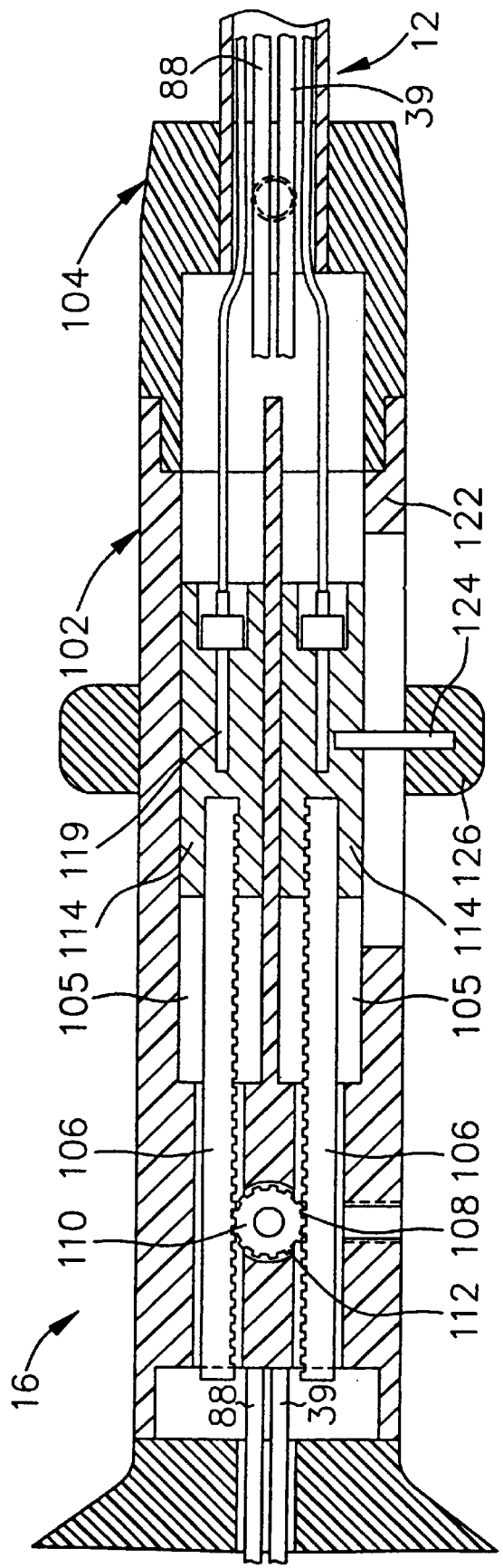
FIG. 10 is a side cross-sectional view of a bidirectional control handle according to the invention.

An alternative control handle 16 particularly suitable for the bidirectional catheter embodiment of the invention is illustrated in FIG. 10. The control handle 16 comprises a generally solid and generally cylindrical housing 102 having a nose piece 104 at its distal end. The housing 102 and nose piece 104 can be made of any suitable material, preferably acetal. The catheter body 12 is fixedly attached to the nose piece 104 by means of a shrink sleeve, as described above.

Within the housing 102 are two rack gear channels 105. Preferably the rack gear channels 105 are located in opposite quadrants within the housing 102. Slidably mounted within each rack gear channel 105 is a rack gear 106. Each rack gear 106 is generally rectangular having teeth 108 along the length of its interior edge. Between the rack gears 106 is a spur gear 110, also having teeth 112. The teeth 112 of the spur gear 110 receive the teeth 108 of the rack gears 106 such that proximal movement off one rack gear results in distal movement of the other rack gear.

The proximal end of each puller wire 42 is attached to the distal end of one of the rack gears 106 by a puller wire coupling 114. The coupling 114 may be integral with the rack gear 106 or fixedly attached to it. Each rack gear 106 may be soldered or glued to the coupling 114, for example, with polyurethane or epoxy. Alternatively, the proximal end of each puller wire coupling 114 may comprise a threaded hole to receive a threaded post at the distal end of the corresponding rack gear 106. The couplings 114 can be made of any suitable material, preferably aluminum.

Figure 11:
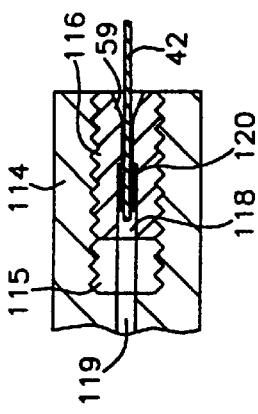
FIG. 11 is a side cross-sectional view of a preferred means for securing the puller wires to the control handle.

As shown in FIG. 11, the distal end of each coupling 114 contains a threaded axial hole 115 that receives a threaded set screw 116. The set screw 116 has an axial bore 118 therethrough for passage of the proximal end of the puller wire 42. In a preferred embodiment, the axial bore 118 has a distal section with a diameter slightly larger than the diameter of the puller wire 42 and a proximal section having a diameter larger than that of the distal section. The axial bore 118 extends through the proximal end of the set screw 116.

The puller wire 42 extends through the axial bore 118 of the set screw 116 and is anchored thereto. A preferred means for anchoring the puller wire 42 to the set screw 116 comprises a short piece of hypodermic stock 120 that is fixedly attached, i.e., by crimping, to the proximal end of the puller wire 42 after it has passed through the distal section of the axial bore 118 of the set screw 116. The hypodermic stock 120 has a diameter greater than the diameter of the distal section of the axial bore 118 and prevents the puller wire 42 from being pulled through the set screw 116. As an alternative, a cross-member, e.g., stainless steel ribbon, may be welded to the proximal end of the puller wire 42 such that the cross-member prevents the puller wire from being pulled through the axial bore 118 of the set screw 116. It is understood that any mechanism for attaching the proximal end of the puller wire to the coupling 114 may be used.

Within the coupling 114 is an axial hole 119, which has a diameter similar to the distal end of the axial bore 118 in the set screw 116. The distal end of the axial hole 119 is in communication with the proximal end of the axial bore 118 to provide a passage into which the puller wire 42 can extend when the corresponding rack gear 106 and coupling 114 are moved distally. This prevents the puller wire 42 from buckling.

The handle housing 102 contains a slot 122 along one side, corresponding with the position of one of the rack gears 106. A lever is attached to the rack gear 106 closest to the slot 122 and extends out of the slot to allow the user to slide the rack gear by moving the lever, in the depicted embodiment, the lever comprises a set screw 124, or other mounting means such as a rivet or stud, which extends through the slot 122 into the rack gear 106 through the puller wire coupling 114. A deflection knob 126 is placed on the outside end of the set screw 124 for easy manipulation of the control handle 16. The deflection knob 126 extends around the circumference of the handle housing 102, allowing the user to manipulate the knob 126 no matter how the handle is turned. Preferably the set screw 124 is positioned on the rack gear 106 so that when both rack gears 106 are in a neutral position, i.e., in line with each other, the deflection knob 126 is situated approximately at the midsection of the slot 122.

When the deflection knob 126 is moved proximally, the corresponding rack gear 106 moves in a proximal direction. The attached puller wire 42 also is pulled proximally, causing the tip section 14 to deflect in the direction of the quadrant of the lumen in the tip section 14 through which that puller wire extends. Conversely, when the deflection knob 126 is pushed distally, the corresponding rack gear 106 moves distally. As a result, the opposite rack gear 106 moves proximally, pulling the corresponding puller wire 42 and deflecting the tip section 14 in the opposite direction.

Passages are provided within the handle housing 102 for the infusion tube 88, lead wires 40, thermocouple wires 41 and 45 and sensor cable 74 to extend through the housing 102 and out the distal end. The infusion tube 88, lead wires 40, thermocouple wires 41 and 45 and sensor cable 74 extend out the proximal end of the handle housing 102 and attached to a luer hub or to appropriate monitors, as described above.

Figure 12:
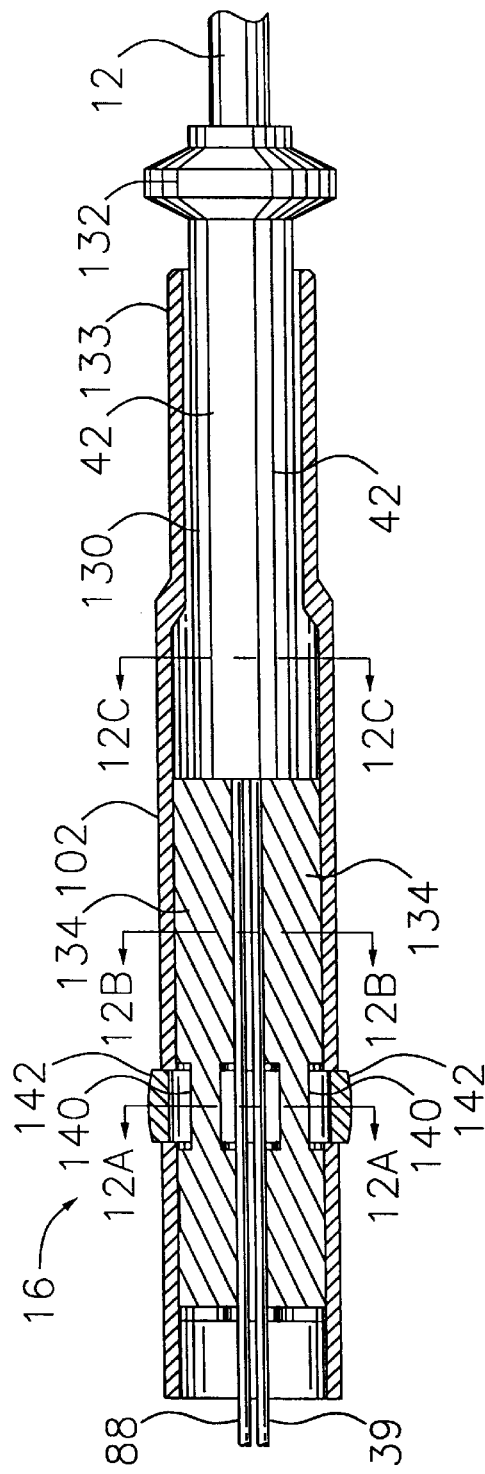
FIG. 12 is a side cross-sectional view of an alternative bidirectional control handle according to the invention.
Figure 13:
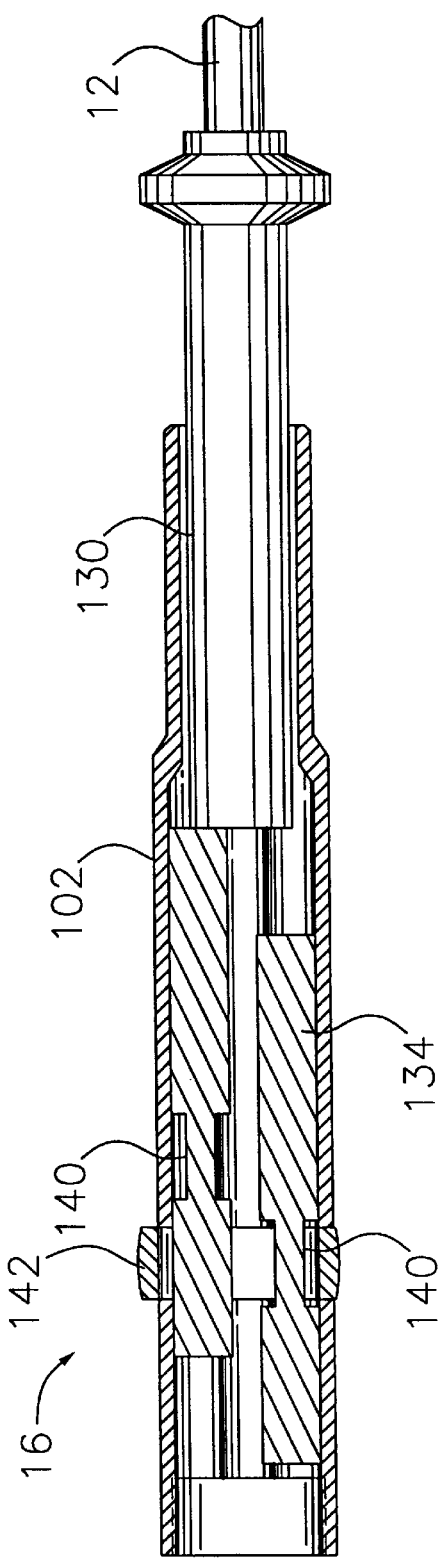
FIG. 13 is a side cross-sectional view of the bidirectional control handle of FIG. 12 where the piston is extended distally with respect to the handle housing.

Another alternative bidirectional handle design is illustrated in FIGS. 12 and 13. As shown in FIGS. 12, 12A, 12B and 12C, the control handle 16 comprises a generally tubular handle housing 102, which can be made of any suitable rigid material. The housing 102 comprises three piston chambers, an axial distal piston chamber 131 and two smaller proximal piston chambers 135. The proximal piston chambers 135 are preferably in opposite quadrants of the housing and overlap the distal piston chamber 131. Mounted within the distal piston chamber 131 and extending out of the distal end of the housing 102 is a slidable distal piston 130 having a thumb rest 132 at its distal end and an axial passage 133. The proximal end of the catheter body 12 is attached, e.g., by glue, to the distal piston 130. The protective sheath 39 containing the puller wires 42, lead wires 40, thermocouple wires 41 and 45, and the first infusion tube 88 extend through the axial passage 133 of the distal piston 130. Proximal to the distal piston 130, two slidable proximal pistons 134 are located in the proximal piston chambers 135. The proximal pistons 134 can be made of any suitable material. Aluminum is presently preferred. Each puller wire 42 is anchored at its proximal end to the distal end of a proximal piston 134. The puller wires 42 can be fixedly attached to the proximal pistons 134 by any suitable means, for example, by means of a coupling as described above.

In this arrangement, distal movement of the distal piston 130 relative to the handle housing 102 by pushing on the thumb rest 132 also results in distal movement of the catheter body 12, the puller wires 42 and the proximal pistons 134 to which the puller wires are attached. Tip deflection does not occur however when both puller wires are moved simultaneously. Accordingly, means are provided for preventing simultaneous movement of the puller wires.

The means for preventing simultaneous movement of the puller wires 42 comprises means for anchoring, i.e., preventing movement of, one, but not both, of the proximal pistons 134. This is done by the combination of a circumferential notch 140 along the length of each proximal piston 134 and a means for engaging the circumferential notch 140 of a selected one of the proximal pistons 134.

Figure 12A:
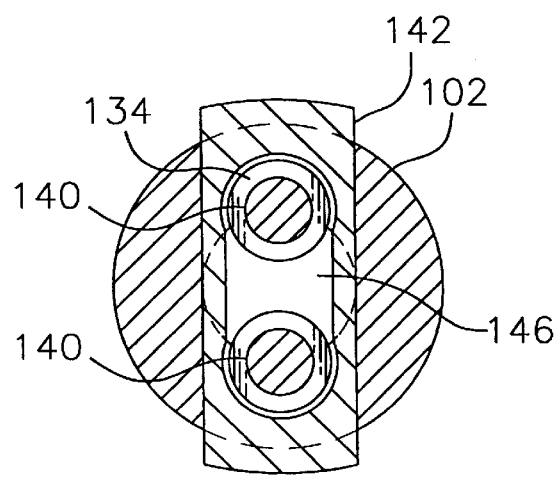
FIG. 12A is a longitudinal cross-sectional view of the bidirectional control handle of FIG. 12 along line 12A—12A.
Figure 12B:
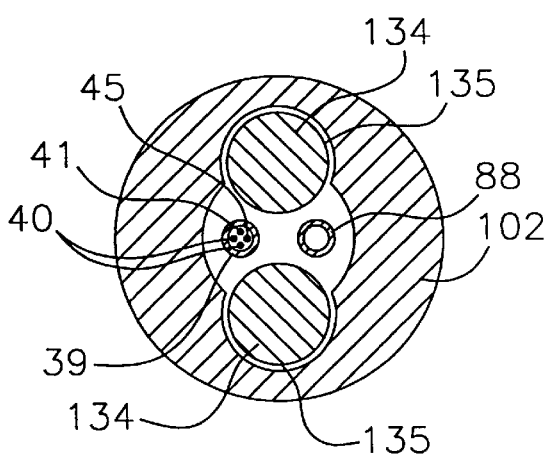
FIG. 12B is a longitudinal cross-sectional view of the bidirectional control handle of FIG. 12 along line 12B—12B.
Figure 13A:
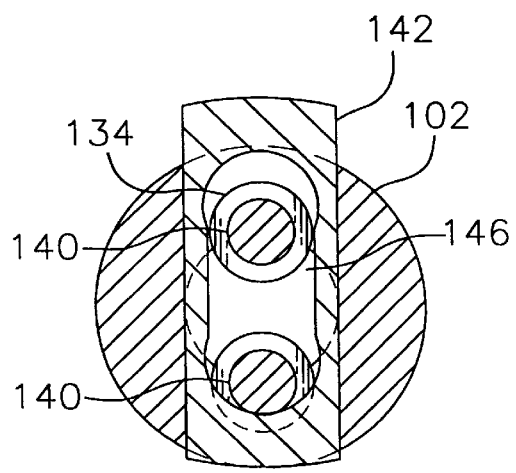
FIG. 13A is a longitudinal cross-sectional view of the bidirectional control handle of FIG. 13 along line 13A—13A.
Figure 12C:
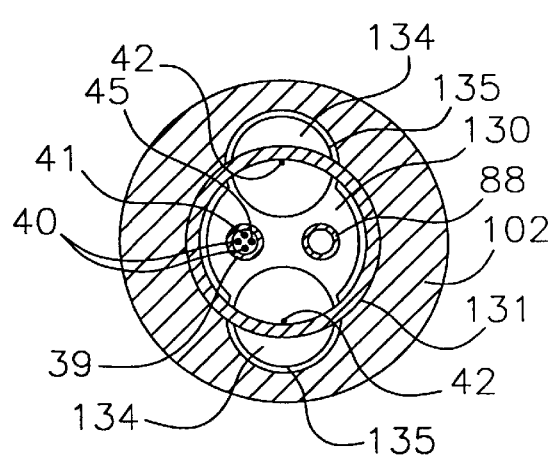
FIG. 12C is a longitudinal cross-sectional view of the bidirectional control handle of FIG. 12 along line 12C—12C.

A preferred engaging means comprises a movable bar 142 which extends diametrically through the handle housing 102 and extends slightly out of the housing on each side to thereby create what appears to be a button on each side of the housing at a position corresponding to the circumferential notches 104 of the proximal pistons 134 as shown in FIGS. 12 and 12A. As shown in FIGS. 13 and 13A, the bar 142 comprises a generally oval slot 146. Both of the proximal pistons 134 extend through the slot 146. The slot 146 has a width slightly greater than the diameter of the proximal pistons 134. The height of the bar 142 is less than the length of the circumferential notches 140 so that the bar 142 can be received by and engages the notches 140. The length of the slot 146 is selected to allow lengthwise movement of only one proximal piston 134 at a time. That is, as shown in FIG. 13, the bar 142 has been moved in a first direction until the end of the slot 146 engages the circumferential notch of one proximal piston 134. In this arrangement, the engaged proximal piston is prevented from moving longitudinally by the bar 142, but the other proximal piston can move freely through the slot 146. If the bar 142 is moved in the other direction the previously engaged proximal piston will be afforded free longitudinal movement and the previously freely moving proximal piston will be engaged.

When a proximal piston 134 is engaged by the bar 142, it acts as a fixed anchor for the puller wire 42 attached to it. Hence when the distal piston 130 is moved distally relative to the housing 102 by pushing the thumb rest 132, the catheter body 12 will move distally relative to the anchored puller wire 42. This results in deflection of the tip section 14 in the direction of the tip lumen carrying that puller wire. When the opposite proximal piston is engaged, deflection of the tip in the opposite direction will occur.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bi-directionsl steerable catheter comprising:
   a catheter body having a tubular wall, proximal and distal ends, and at least one lumen extending therethrough;
   a tip section comprising flexible tubing having proximal and distal ends and at least one lumen extending therethrough, the proximal end of the tip section being fixedly attached to the distal end of the catheter body;
   a control handle mounted at its distal end to the proximal end of the catheter body comprising:
      a housing having proximal and distal ends;
      a generally-circular spur gear rotatably mounted within the housing, the spur gear having gear teeth about its outer circumference;
      a pair of spaced apart rack gears slidably mounted longitudinally on diametrically opposed sides of the spur gear within the housing, each rack gear having an interior edge generally facing the interior edge of the other rack gear and comprising gear teeth along its interior edge for engaging the gear teeth of the spur gear, each rack gear being longitudinally movable between first and second positions, whereby proximal movement of one rack gear results in rotational movement of the spur gear and distal movement of the other rack gear; and
      a manually movable member fixedly attached to one rack gear and extending radially out of the housing through a slot in the housing; and
   a pair of puller wires having proximal and distal ends, each puller wire extending from the control handle through a lumen in the catheter body and into an off axis lumen in the tip section, the distal end of each puller wire being fixedly attached to the tip section and the proximal end of each puller wire being anchored to a separate associated rack gear in the control handle whereby proximal movement of a rack gear and its associated puller wire relative to the catheter body results in deflection of the tip section in the direction of the off axis lumen into which that puller wire extends.

2. A catheter according to claim 1, wherein each puller wire is anchored to its associated rack gear by a puller wire coupling mounted at the distal end of the rack gear, the puller wire coupling comprising:
   a threaded set screw having an axial bore therethrough through which the proximal end of the puller wire extends;
   means for anchoring the proximal end of the puller wire to the threaded set screw; and
   a threaded axial hole in the distal end of the rack gear for receiving the threaded set screw.

3. A catheter according to claim 2, wherein the anchoring means comprises a piece of hypodermic stock fixedly attached to the proximal end of the puller wire, said hypodermic stock having an outer diameter greater than the diameter of the axial bore of the set screw.

4. A catheter according to claim 1, wherein the tip section further comprises a tip electrode mounted at the distal end of the flexible tubing.

5. A catheter according to claim 4, wherein the puller wires are anchored at their distal ends to the tip electrode.

6. A catheter according to claim 1, wherein the puller wires are anchored at their distal ends to the flexible tubing.

7. A catheter according to claim 1, wherein the rack gears are slidably movable within rack gear channels within the handle housing.

8. A catheter according to claim 1 wherein each rack gear contains a bore for receiving the proximal end of the puller wire associated with that rack gear when that rack gear is moved distally relative to the catheter body.

9. A catheter according to claim 1, wherein the catheter body has a single lumen.

10. A catheter according to claim 9, further comprising two compression coils extending through the catheter body, each in surrounding relation to a corresponding puller wire.

11. A catheter according to claim 10, wherein the catheter body has a single lumen.

12. A catheter according to claim 11, further comprising two compression coils extending through the catheter body each in surrounding relation to a corresponding puller wire.

13. A bi-directional steerable catheter comprising:
a catheter body having an outer wall, proximal and distal ends, and at least one lumen extending therethrough;
a tip section comprising flexible tubing having proximal and distal ends and at least one lumen extending therethrough, the proximal end of the tip section being fixedly attached to the distal end of the catheter body;
a control handle comprising a housing having proximal and distal ends, the handle being mounted at its distal end to the proximal end of the catheter body and containing:
two off-axis rack gear channels,
a rack gear slidably mounted within each rack gear channel, each rack gear having an interior edge generally facing the interior edge of the other rack gear and each rack gear having teeth along its interior edge,
a generally-circular spur gear mounted between the rack gears, the spur gear having teeth around its circumference capable of receiving the teeth of the rack gears, whereby proximal movement of one rack gear results in rotational movement of the spur gear and distal movement of the other rack gear; and
a manually movable member fixedly attached to one rack gear and extending radially out of the housing through a slot in the housing; and
two puller wires having proximal and distal ends and extending through a lumen in the catheter body and a lumen in the tip section, the distal end of each puller wire being fixedly attached to the tip section and the proximal end of each puller wire being anchored to a separate rack gear in the control handle;
whereby proximal movement of a rack gear relative to the catheter body results in deflection of the tip section on the side to which the puller wire connected to the proximally-moved rack gear is attached.

14. A catheter according to claim 13, wherein each puller wire is anchored to its associated rack gear by a puller wire coupling mounted at the distal end of the rack gear, the puller wire coupling comprising:
a threaded set screw having an axial bore therethrough through which the proximal end of the puller wire extends;
means for anchoring the proximal end of the puller wire to the threaded set screw; and
a threaded axial hole in the distal end of the rack gear for receiving the threaded set screw.

15. A catheter according to claim 14, wherein the anchoring means comprises a piece of hypodermic stock fixedly attached to the proximal end of the puller wire, said hypodermic stock having an outer diameter greater than the diameter of the axial hole of the set screw.

16. A catheter according to claim 13, wherein the tip section further comprises a tip electrode mounted at the distal end of the flexible tubing.

17. A catheter according to claim 16, wherein the puller wires are anchored at their distal ends to the tip electrode.

18. A catheter according to claim 13, wherein the puller wires are anchored at their distal ends to the flexible tubing.

19. A catheter according to claim 13, wherein the rack gear channels are located in opposite quadrants within the housing.

20. A bi-directional steerable catheter comprising:
a catheter body having a tubular wall, proximal and distal ends, and at least one lumen extending therethrough;
a tip section comprising flexible tubing having proximal and distal ends and at least one lumen extending therethrough, the proximal end of the tip section being fixedly attached to the distal end of the catheter body;
a control handle mounted at its distal end to the proximal end of the catheter body comprising:
a housing having proximal and distal ends;
a generally-circular spur gear rotatably mounted within the housing, the spur gear having gear teeth about its outer circumference;
a pair of spaced apart rack gears slidably mounted longitudinally on diametrically opposed sides of the spur gear within the housing, each rack gear having an interior edge generally facing the interior edge of the other rack gear and comprising gear teeth along its interior edge for engaging the gear teeth of the spur gear, each rack gear being longitudinally movable between first and second positions, whereby proximal movement of one rack gear results in rotational movement of the spur gear and distal movement of the other rack gear; and
a manually movable member fixedly attached to one rack gear in perpendicular relation to the attached rack gear; and
a pair of puller wires having proximal and distal ends, each puller wire extending from the control handle through a lumen in the catheter body and into an off axis lumen in the tip section, the distal end of each puller wire being fixedly attached to the tip section and the proximal end of each puller wire being anchored to a separate associated rack gear in the control handle whereby proximal movement of a rack gear and its associated puller wire relative to the catheter body results in deflection of the tip section in the direction of the off axis lumen into which that puller wire extends.

21. A catheter according to claim 20, wherein each puller wire is anchored to its associated rack gear by a puller wire coupling mounted at the distal end of the rack gear, the puller wire coupling comprising:
a threaded set screw having an axial hole therethrough through which the proximal end of the puller wire extends;
means for anchoring the proximal end of the puller wire to the threaded set screw; and
a threaded axial hole in the distal end of the rack gear for receiving the threaded set screw.

22. A catheter according to claim 20, wherein each rack gear contains a bore for receiving the proximal end of the puller wire associated with that rack gear when that rack gear is moved distally relative to the catheter body.

* * * * *

UNITED STATES PATENT AND TRADEMARK OFFICE
CERTIFICATE OF CORRECTION

PATENT NO.    : 6,171,277 B1
DATED         : January 9, 2001
INVENTOR(S)   : Dean M. Ponzi It is certified that error appears in the above-identified patent and that said Letters Patent is hereby corrected as shown below:

Column 13,
Line 61, replace "bi-directionsl" with -- bi-directional --.

Column 14,
Line 66, replace "claim 10" with -- claim 13 --.

Signed and Sealed this

Second Day of July, 2002

Attest:

JAMES E. ROGAN
Attesting Officer          Director of the United States Patent and Trademark Office